US008571682B2

(12) United States Patent
Arisso et al.

(10) Patent No.: US 8,571,682 B2
(45) Date of Patent: Oct. 29, 2013

(54) CONNECTING APPARATUS AND METHODS

(75) Inventors: Luis M. Arisso, Fox Point, WI (US); Lawrence D. Swanson, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 806 days.

(21) Appl. No.: 12/099,955

(22) Filed: Apr. 9, 2008

(65) Prior Publication Data
US 2008/0255630 A1    Oct. 16, 2008

Related U.S. Application Data

(60) Provisional application No. 60/911,172, filed on Apr. 11, 2007.

(51) Int. Cl.
*A61N 1/05* (2006.01)

(52) U.S. Cl.
USPC ............................................. 607/116

(58) Field of Classification Search
USPC ............................ 607/36–38, 115–118
See application file for complete search history.

(56) References Cited

U.S. PATENT DOCUMENTS

| 4,627,439 | A | * | 12/1986 | Harris ........................ 166/272.5 |
| 5,413,595 | A | | 5/1995 | Stutz |
| 5,679,026 | A | | 10/1997 | Fain et al. |
| 6,743,055 | B1 | | 6/2004 | Flynn et al. |
| 7,130,699 | B2 | * | 10/2006 | Huff et al. ....................... 607/116 |
| 7,155,280 | B2 | | 12/2006 | Daum et al. |
| 7,171,260 | B2 | | 1/2007 | Lee et al. |
| 2004/0230267 | A1 | * | 11/2004 | Wenger ........................ 607/116 |
| 2006/0030918 | A1 | * | 2/2006 | Chinn et al. ................... 607/117 |
| 2006/0271136 | A1 | * | 11/2006 | Wojciechowicz ............. 607/116 |

* cited by examiner

*Primary Examiner* — Rex R Holmes
(74) *Attorney, Agent, or Firm* — Pauly, Devries Smith & Deffner, L.L.C.

(57) ABSTRACT

Included herein, amongst other things, is a stimulation lead adapter. The stimulation lead adapter can include a stimulation lead socket configured to electrically engage and retain the proximal end of a stimulation lead. The stimulation lead adapter can also include an adapter plug configured to electrically engage a stimulation lead port of an implantable medical device. The stimulation lead adapter can also include a connector configured to provide electrical communication between the stimulation lead socket and the adapter plug. In an embodiment, the invention includes an implantable cardiac rhythm management device configured to perform at least one pacing system analyzer function. In an embodiment, the invention includes a programmer system for an implantable medical device, the programmer system configured to display pacing system analyzer function data within a single tabbed window of a graphical user interface. Other aspects and embodiments are also provided herein.

13 Claims, 14 Drawing Sheets

CONNECTING APPARATUS AND METHODS

This application claims the benefit of U.S. Provisional Application No. 60/911,172, filed Apr. 11, 2007, the content of which is herein incorporated by reference.

FIELD OF THE INVENTION

This disclosure relates generally to a connecting apparatus and, more particularly, to a connecting apparatus for an implantable medical device and related devices and methods.

BACKGROUND OF THE INVENTION

Implantable medical devices (IMDs) are commonly used to provide treatment to patients. By way of example, implantable medical devices can include cardiac rhythm management devices and neurological stimulation devices, amongst others. Some implantable medical devices are configured to deliver electrical stimuli to a target tissue, such as in the heart or nervous system, via a stimulation lead having one or more electrodes disposed in or about the target tissue. The stimulation lead is frequently connected to a pulse generator housing via an assembly commonly referred to as a header. The header serves to provide fixation of the proximal end of the lead and electrically couples the lead with the pulse generator.

During the procedure of implanting the medical device, the leads are generally threaded through a major vein (typically the subclavian vein) in the upper chest and into the heart with the help of imaging devices. The leads are manipulated using a stylet disposed within a lumen of the leads. Generally, the leads are then connected to an external (non-implantable) testing and temporary pacing device known as a pacing system analyzer (PSA). The PSA can run tests to ensure adequate lead placement, temporarily maintain basic cardiac functions, and/or evaluate pacing parameters to support an initial programming of the implantable medical device. Using the PSA, various pacing modes and/or parameters are evaluated to determine whether the leads are properly placed and to determine a set of suitable pacing parameters. After tests with the PSA are completed and the distal ends of the leads are in the proper position, the PSA is disconnected, the stylet is removed from the lumen of the stimulation leads, and the proximal ends of the stimulation leads are attached to the pulse generator, such as via the header. Specifically, the proximal ends of the leads are inserted into ports in the header and then secured in place with a fastener (such as a set screw), an adhesive, or a compression type fitting.

However, the use of a PSA system requires having and maintaining another complex and expensive piece of equipment. For at least this reason, a need exists for additional methods and systems for performing the functions of a pacing system analyzer.

SUMMARY OF THE INVENTION

Amongst other things, this disclosure relates to a connecting apparatus for an implantable medical device that can allow a stimulation lead to be connected to a header without removing a stylet or guide wire from the stimulation lead. This disclosure also relates to an implantable medical device that can perform functions of a pacing system analyzer (PSA) and a programmer system configured to display pacing system analyzer function data.

In an embodiment, the invention includes a stimulation lead adapter. The stimulation lead adapter can include a stimulation lead socket configured to electrically engage and retain the proximal end of a stimulation lead. The stimulation lead adapter can also include an adapter plug configured to electrically engage a stimulation lead port of an implantable medical device. The stimulation lead adapter can also include a connector configured to provide electrical communication between the stimulation lead socket and the adapter plug and allow movement of the adapter plug independent of the stimulation lead socket.

In an embodiment, the invention includes a stimulation lead adapter including a receptacle housing. The receptacle housing can include a lead socket, the lead socket having a first end and a second end disposed on opposite sides of a lengthwise major axis. The lead socket can define a first aperture in the first end and a second aperture in the second end. The lead socket can further define a side wall connecting the first end with the second end. A first electrical contact can be disposed along the side wall of the lead socket. The stimulation lead adapter can also include an adapter plug and a second electrical contact disposed on the adapter plug. The stimulation lead adapter can also include a conductor providing electrical communication between the first electrical contact and the second electrical contact.

In an embodiment, the invention includes an implantable cardiac rhythm management device including a housing and circuitry disposed within the housing, the circuitry including an ventricular channel interface and a controller in communication with the ventricular channel interface. The implantable cardiac rhythm management device can be configured to perform at least one pacing system analyzer function.

In an embodiment, the invention includes a programmer system for an implantable medical device, the programmer system including a microprocessor, a telemetry interface in communication with the microprocessor, the telemetry interface configured to provide wireless communication with the implantable medical device. The programmer system can be configured to display pacing system analyzer function data within a single tabbed window of a graphical user interface.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

A pacing system analyzer (PSA) is a device that can be used to aid in the implantation of stimulation leads and an implantable cardiac rhythm management device. PSAs can run various tests to ensure adequate lead placement, can temporarily maintain basic cardiac functions, and/or can evaluate pacing parameters to support an initial programming of the implantable medical device.

It is disclosed herein that the cardiac rhythm management device to be implanted can itself be used to perform functions currently performed by PSA systems. Specifically, by connecting a stimulation lead (or "lead") to an implantable cardiac rhythm management device via a stimulation lead connection adapter, it is possible to avoid using a PSA system during the implantation procedure. In some embodiments, the invention includes a stimulation lead connection adapter. In some embodiments, the invention includes an implantable cardiac rhythm management device that is configured to perform PSA functions. In some embodiments, the invention includes a programmer system for an implantable cardiac rhythm management device that is configured to display PSA function data within a single tabbed window.

Figure 1:
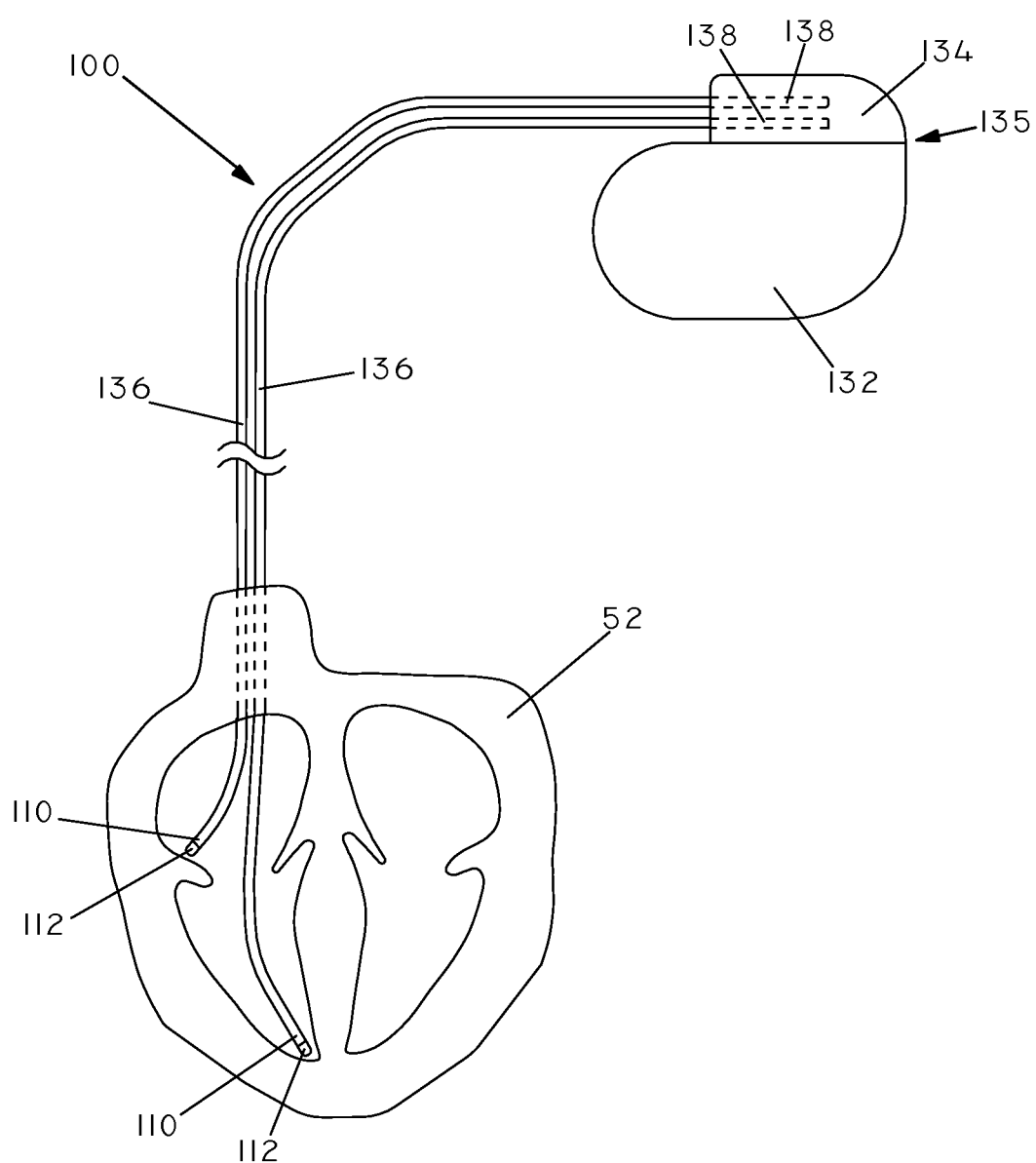
FIG. 1 is a schematic view of an implantable medical system.

Referring now to FIG. 1, a schematic view is shown of an implantable medical system 100. In various embodiments, the implantable medical system 100 can include a cardiac rhythm management device, such as a pacemaker, a cardiac resynchronization therapy (CRT) device, a remodeling control therapy (RCT) device, a cardioverter/defibrillator, or a pacemaker-cardioverter/defibrillator. In some embodiments, the implantable medical device 100 can include a neurological stimulation device. The term "pulse generator" as used herein shall refer to the part or parts of an implanted medical device, such as a cardiac rhythm management device or a neurological therapy device, containing the power source and circuitry for delivering pacing therapy, electrical stimulation, and/or shock therapy. It will be appreciated that embodiments of the invention can also be used in conjunction with implantable medical devices that lack pulse generators such as monitoring devices and drug delivery devices.

The implantable medical system 100 includes an implantable medical device 135 and one or more stimulation leads 136. The implantable medical device can include a pulse generator 132 and a header 134. The proximal ends 138 of the stimulation leads 136 are disposed within the header 134. The stimulation leads 136 transvenously pass to the heart 52 where the distal ends 110 of the stimulation leads 136 include electrodes 112. Depending on the configuration, the stimulation leads 136 can provide electrical and/or optical communication between the distal ends of the stimulation leads 136 and the pulse generator 132. In operation, the pulse generator 132 may generate pacing pulses or therapeutic shocks which are delivered to the heart 52 via the stimulation leads 136. In many embodiments, the stimulation leads 136 include a material that is electrically conductive in order to deliver the pacing pulses or therapeutic shocks.

The implantable medical system 100 is implanted into a patient during a surgical procedure. This procedure can include many different steps. Typically, however, the stimulation leads 136 are threaded through a major vein (such as the subclavian vein) in the upper chest and into the heart with the help of imaging devices. Usually, a stylet disposed within a lumen of the stimulation leads 136 is used to help guide the stimulation leads 136 to the heart 52. Because of various reasons, including physiological differences between patients and variation regarding the actual placement of the electrodes within the heart, the stimulation leads 136 are frequently tested after placement within the patient. Sometimes, the stimulation leads 136 are repositioned after placement and therefore it is desirable to leave the stylet within the lumen of the stimulation leads 136 until testing of the leads 136 is complete.

A specialized system known as pacing system analyzer (PSA) is frequently used during the implantation of CRM devices in order to perform testing on the stimulation leads and evaluate pacing parameters to support an initial programming of the implantable medical system. A PSA can also perform other functions such as maintaining basic cardiac functions by administering temporary pacing therapy before the stimulation leads are connected to the pulse generator.

However, there are inherent issues associated with relying on the measurements taken by PSA systems. Logically, measurements are influenced by the circuitry in the system used to take the measurements and the circuitry in a PSA system may be quite different from the circuitry in a given implanted medical device. This is compounded by the fact that there are many different types of implanted devices made by many different manufacturers, each with unique circuit designs. As such, the testing and measurement performed with a PSA system does not always accurately reflect what will be observed after a specific implantable medical device is implanted.

In addition, the use of a PSA system requires having and maintaining another complex and expensive piece of equipment. Finally, as new implanted medical devices incorporate new features, there is a need to update the capabilities of the PSA systems so that they can provide measurement and testing to support these new features.

In some embodiments, the present invention includes a stimulation lead connection adapter that can facilitate connection of the proximal ends of the leads to the header without removing the stylet from the stimulation leads. In such an embodiment, the pulse generator can be configured to perform testing such as that normally performed by a PSA. By using a pulse generator to perform testing, there is no need for a separate PSA and the issues referenced above can be avoided.

Figure 2:
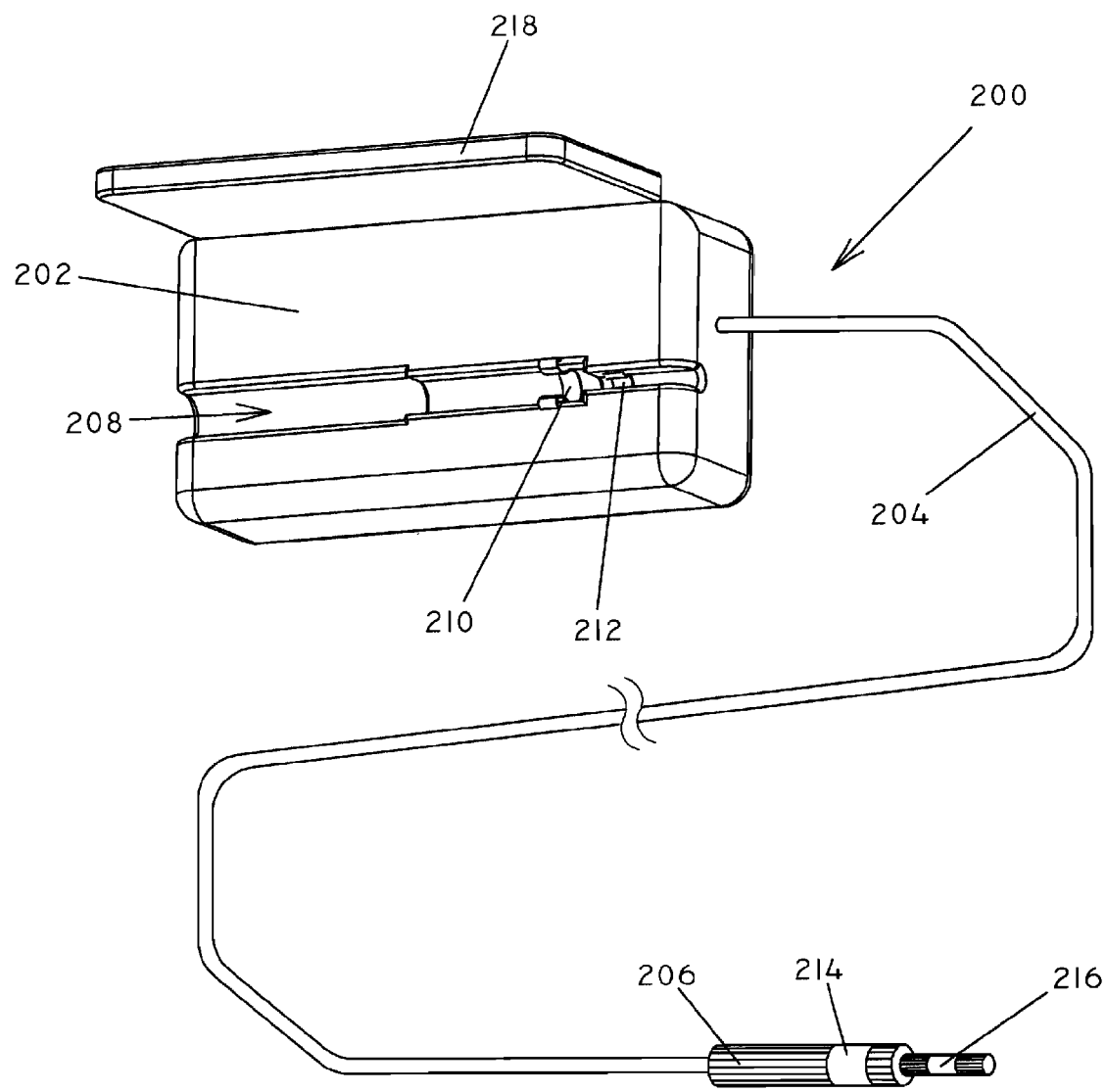
FIG. 2 is a schematic view of a stimulation lead connection adapter.

Referring now to FIG. 2, a schematic view of a stimulation lead connection adapter 200 is shown in accordance with an embodiment of the invention. A housing 202 includes a lead socket 208. The housing may be made of various materials including polymers, metals, ceramics and the like. The lead socket 208 can also be made of various materials including polymer, metal, ceramics and the like. The lead socket 208 is configured so as to accommodate the proximal end of a stimulation lead. In some embodiments, the lead socket 208 can be configured to electrically engage and retain the proximal end of a stimulation lead.

The lead socket 208 can have various dimensions so as to accommodate the proximal end of different types of stimulation leads. By way of example, the lead socket 208 can have physical dimensions sufficient to accommodate leads conforming to various international standards for the lead/header interface such as the DF-1, VS-1, IS-1 and IS-4 standards, amongst others. These international standards include design requirements that specify the length and diameter of various portions of the cavity in the header that receives the proximal end of the lead. One or more electrical contacts (such as 210 and 212) can be disposed along the lead socket 208 and configured to make contact with conductors on the proximal end of a stimulation lead. The electrical contacts can include a conductive material such as a conductive metal.

The stimulation lead connection adapter 200 can also include an adapter plug 206. The adapter plug 206 can be configured to electrically engage a stimulation lead port of an implantable medical device. The adapter plug 206 can include one or more conductors (such as 214 and 216). The physical dimensions of the adapter plug 206 can be configured to conform to various standards for lead-header interfaces such as the DF-1, VS-1, IS-1 and IS-4 international standards. In some embodiments, the adapter plug 206 is configured so that it can be positioned within a stimulation lead port on an implantable medical device with a minimal amount of insertion force. Minimizing the insertion force can be accomplished in various ways. For example, in some embodiments, the adapter plug 206 has a diameter that is slightly smaller than the proximal end of a stimulation lead that would normally be inserted into a stimulation lead port of an implantable medical device. In some embodiments, the adapter plug 206 lacks sealing elements normally included with the proximal end of a stimulation lead, thereby decreasing the required insertion force.

The stimulation lead connection adapter 200 can also include a connector 204. The connector 204 can include a conductor, such as a wire, and a sheath disposed over the conductor, such as a polymeric sheath. The connector 204 connects the housing 202 and/or the lead socket 208 with an adapter plug 206. The connector 204 can be flexible (or non-rigid) under ambient conditions so as to allow movement of the housing 202 and stimulation lead socket 208 independently of the adapter plug 206. The connector 204 can provide electrical communication between conductors along the lead socket 208 and conductors on the adapter plug 206. For example, the connector 204 can provide electrical communication between conductor 210 and conductor 214. The connector 204 can also provide electrical communication between conductor 212 and conductor 216.

Figure 3:
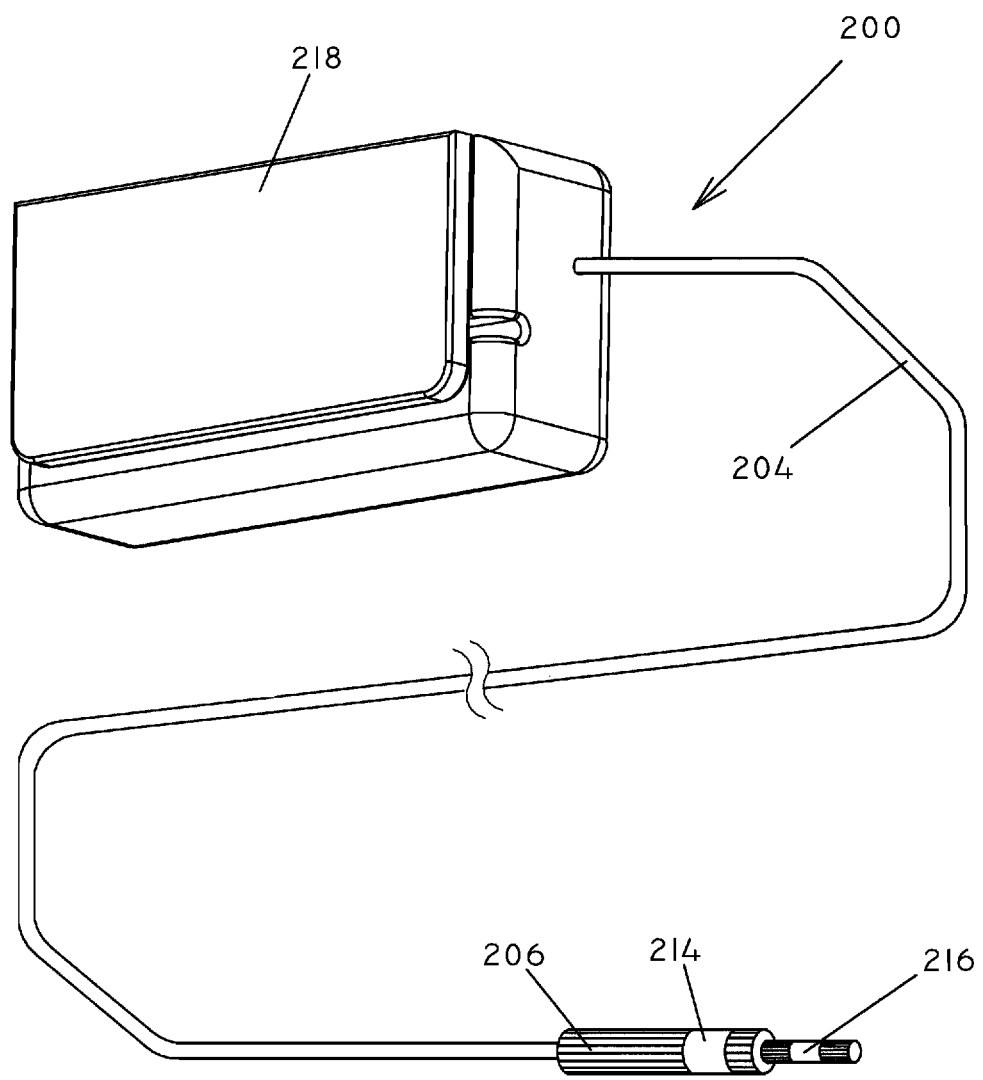
FIG. 3 is a schematic view of the stimulation lead connection adapter of FIG. 2, with the cover in a closed position.

In some cases, it can be desirable to prevent bodily fluids, such as blood, from contacting the electrical contacts of the stimulation lead connection adapter 200. This can be achieved in various ways. In some embodiments, a cover or shroud can be used to protect the electrical contacts of the stimulation lead connection adapter from contact with bodily fluids. For example, the stimulation lead connection adapter 200 of FIG. 2 includes a cover 218 that can be used to prevent bodily fluids from contacting the electrical contacts 210 and 212. The cover 218 can have an open position (as shown in FIG. 2) to accommodate the insertion of the proximal end of a lead into the lead socket 208 and a closed position (as shown in FIG. 3).

Figure 4:
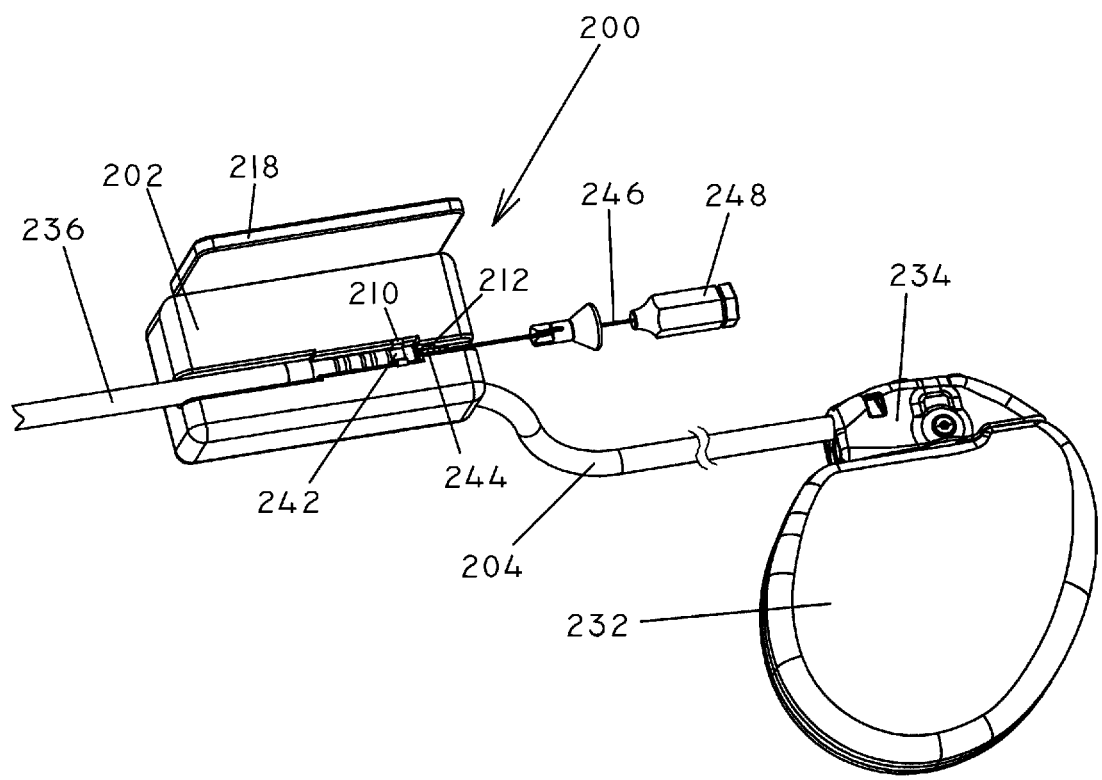
FIG. 4 is a schematic view of a stimulation lead connection adapter in conjunction with a stimulation lead, a header, and a pulse generator.

Referring now to FIG. 4, a schematic view of a stimulation lead adapter 200 is shown as attached to a stimulation lead 236 and a pulse generator 232. Stimulation leads can include a proximal end 236 and a distal end (not shown). The proximal end 236 interfaces with the implanted medical device while the distal end (not shown) can include stimulation electrodes and interfaces with tissue targeted for stimulation. The proximal end 236 of the stimulation lead can include one or more conductors (242 and 244). The proximal end 236 of the stimulation lead can be positioned within the lead socket 208 (shown in FIG. 2) of the stimulation lead connection adapter 200 so as to provide electrical communication between the conductors of the stimulation lead (such as conductors 242 and 244) and the conductors of the connection adapter 200 (such as conductors 210 and 212). The proximal end 236 of the stimulation lead can be secured in the lead socket 208 using various techniques such as with a pressure fitting, a fastener such as a clip, an attachment structure, magnetically, and the like. Lead socket 208 can be configured so that the proximal end 236 of the stimulation lead can be inserted therein and retained, and electrical communication can be established between respective electrical contacts and conductors, with a relatively small insertion force, and without the need to remove a stylet 246 or guide wire and its handle 248 from the stimulation lead 236. The adapter plug 206 (not shown in FIG. 4) of the stimulation lead connection adapter 200 is inserted into a stimulation lead port of a header 234. The header 234 is, in turn, connected to a pulse generator 232 and facilitates electrical communication between the proximal end 236 of the stimulation lead and the pulse generator 232. In some embodiments, the header 234 is configured so as to be able to establish electrical contact with the adapter plug without the need to tighten setscrews. For example, in some embodiments, the header 234 can be equipped with an electrical contact that projects out toward the adapter plug through the force of a spring-type action.

Figure 5:
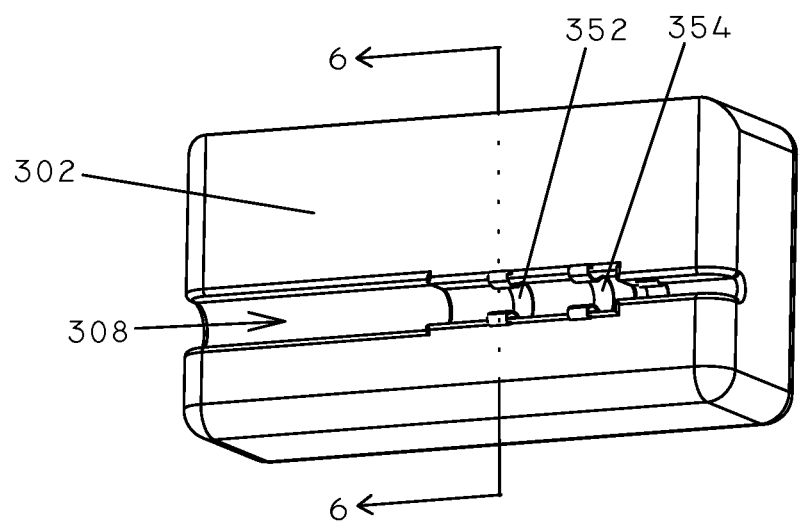
FIG. 5 is a schematic view of a receptacle housing of a stimulation lead connection adapter in accordance with an embodiment of the invention.
Figure 6A:
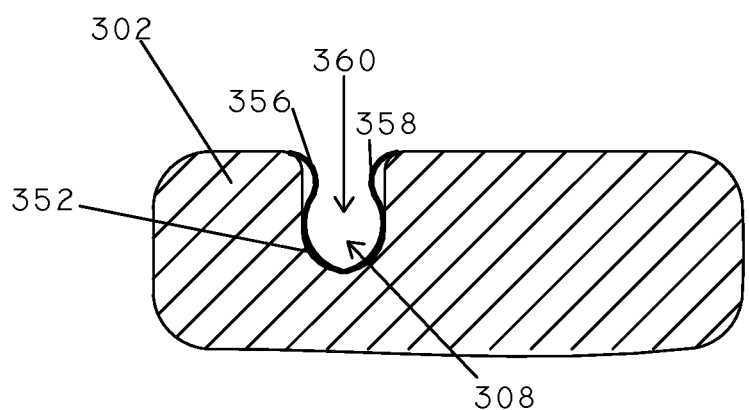
FIG. 6A is a cross-sectional view of the stimulation lead connection adapter of FIG. 5, as taken along line 6-6 of FIG. 5.
Figure 6B:
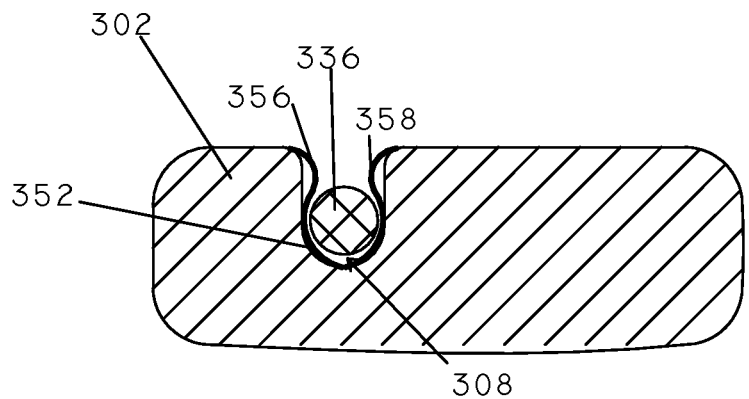
FIG. 6B is a cross-sectional view of the stimulation lead connection adapter of FIG. 5, as taken along line 6-6 of FIG. 5, showing a stimulation lead disposed within a lead socket.

In some embodiments, the stimulation lead adapter can include one or more fasteners or attachment structures in order to secure a stimulation lead to the stimulation lead adapter. Referring now to FIG. 5, a schematic view of a portion of a stimulation lead adapter is shown. The stimulation lead adapter includes a housing 302 and a lead socket 308. A first fastener 352 and a second fastener 354 are disposed along the lead socket 308. The fasteners 352 and 354 can be configured to secure the proximal end of a stimulation lead. Referring now to FIG. 6A, a cross-sectional view is shown of the stimulation lead adapter of FIG. 5, as taken along line 6-6 of FIG. 5. The first fastener 352 includes a first projection 356 and a second projection 358. The distance between the first projection and the second projection is less than the diameter of the lead socket 308. The first projection 356 and second projection 358 can include a flexible material that flexes when an object is pressed into the lead socket 308 in the direction of arrow 360 (perpendicular to the major axis of the lead socket 308). The first projection 356 and second projection 358 can include various flexible materials such as metals, plastics, and the like. Referring now to FIG. 6B, a cross-sectional view is shown of a stimulation lead adapter is shown with a portion of a stimulation lead 336 inserted therein. Specifically, the stimulation lead 336 is disposed within the lead socket 308 and is held in place by the first projection 356 and the second projection 358 of the fastener 352. It will be appreciated that for purposes of simplification of the illustration, certain components, such as electrical conductors, that would normally be visible in a cross-sectional view of a stimulation lead are not shown in FIG. 6B.

It will be appreciated that the fasteners shown in FIGS. 5, 6A, 6B are merely illustrative and that many other fastener designs and fastening mechanisms can be used. In addition, it will be appreciated that in some embodiments, fasteners can also be used as electrical contacts. For example, the fastener can be made of a conductive material and the fastener itself can serve to both retain the stimulation lead as well as provide electrical communication between the stimulation lead and other components of the stimulation lead adapter.

Figure 7:
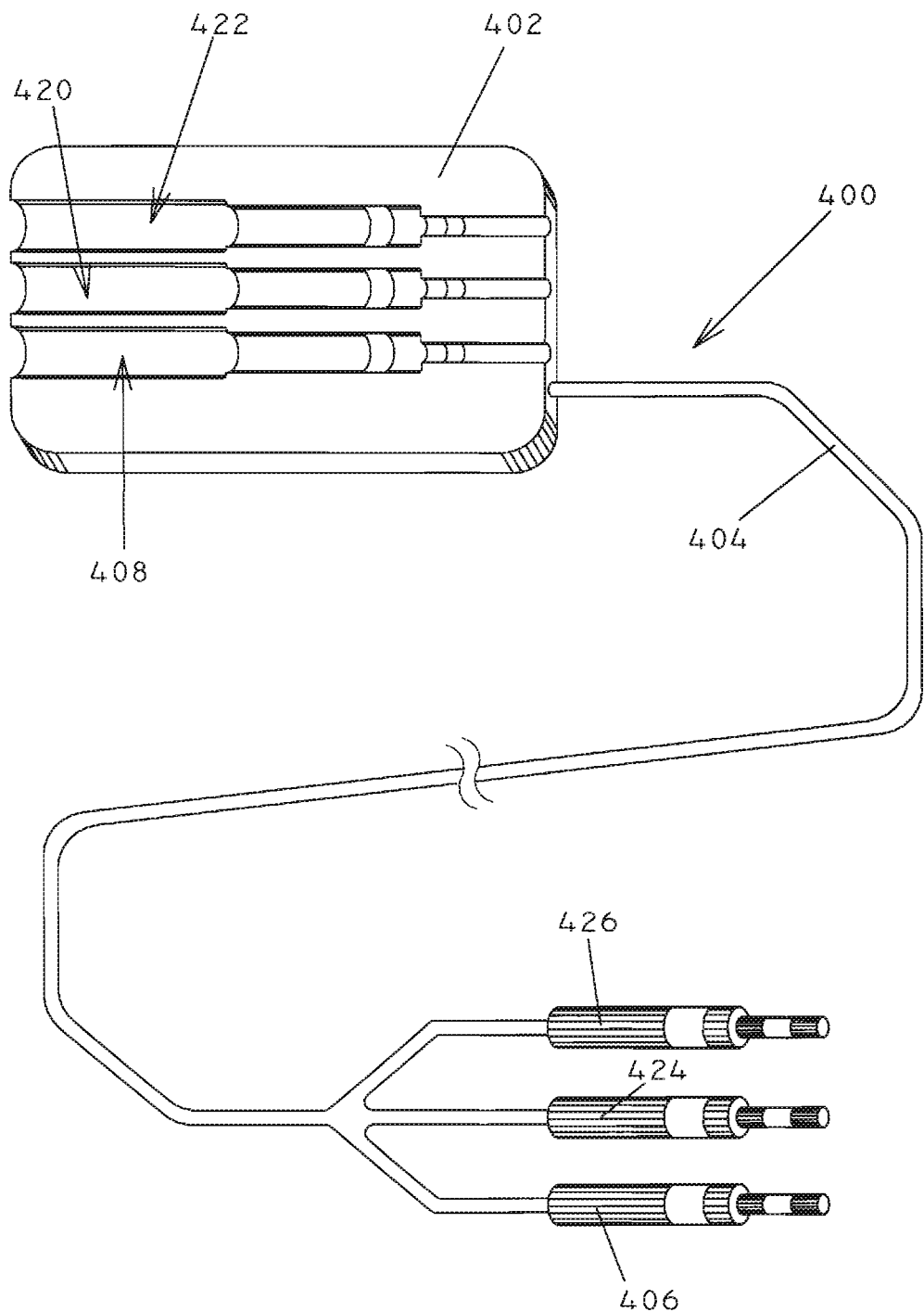
FIG. 7 is a schematic view of a stimulation lead connection adapter in accordance with another embodiment of the invention.

Some stimulation leads may include a plurality of plugs on their proximal end. For example, one plug may be for defibrillation while another might be for atrial pacing and another might be for ventricular pacing. As such, it will be appreciated that stimulation lead connection adapters in accordance with various embodiments of the invention can include a plurality of lead sockets and a plurality of adapter plugs. Referring now to FIG. 7, an embodiment of a stimulation lead connection adapter 400 is shown that includes multiple lead sockets and multiple adapter plugs. A housing 402 defines a first lead socket 408, a second lead socket 420, and a third lead socket 422. The lead sockets 408, 420, and 422 are configured to accommodate plugs from the proximal end of a stimulation lead. A connector 404 connects the housing 402 with a plurality of adapter plugs 406, 424, and 426.

Figure 8:
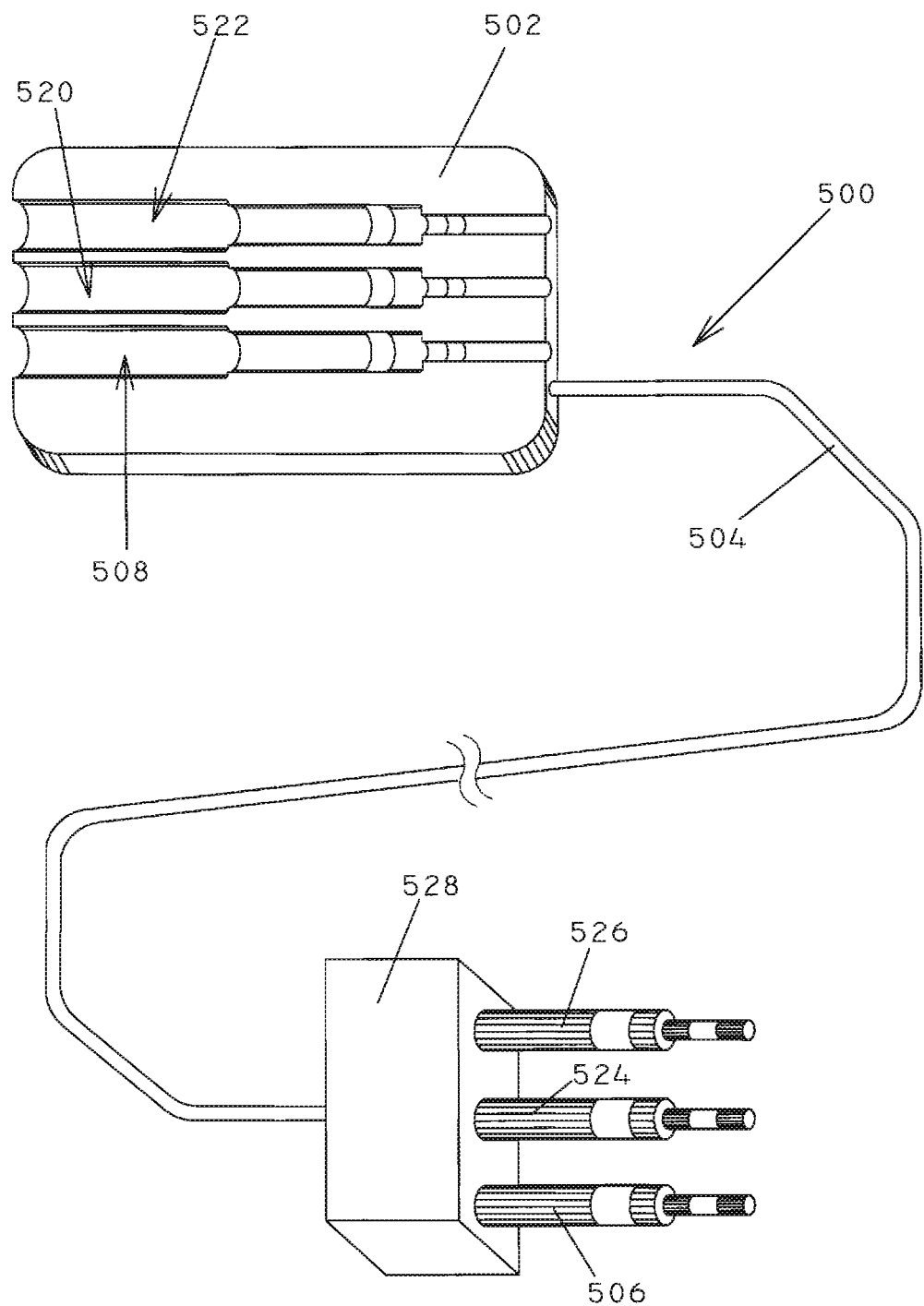
FIG. 8 is a schematic view of a stimulation lead connection adapter in accordance with another embodiment of the invention.

Connecting multiple adapter plugs separately into multiple ports on the header of a CRM device may be inconvenient under some circumstances. As such, in some embodiments, the stimulation lead connection adapter can include an adapter plug manifold retention block that allows multiple adapter plugs to be inserted into a header in one motion. Referring now to FIG. 8, an embodiment of a stimulation lead connection adapter 500 is shown that includes an adapter plug manifold retention block 528. A housing 502 defines a first lead socket 508, a second lead socket 520, and a third lead socket 522. The lead sockets 508, 520, and 522 are configured to accommodate plugs from the proximal ends of a stimulation lead. A connector 504 connects the housing 502 with a plurality of adapter plugs 506, 524, and 526. The adapter plugs are attached to a manifold retention block 528 that maintains the spacing and orientation of the adapter plugs with respect to one another. Specifically, the manifold retention block 528 functions to position the adapter plugs so that they can be easily inserted into the header of a medical device.

Figure 9:
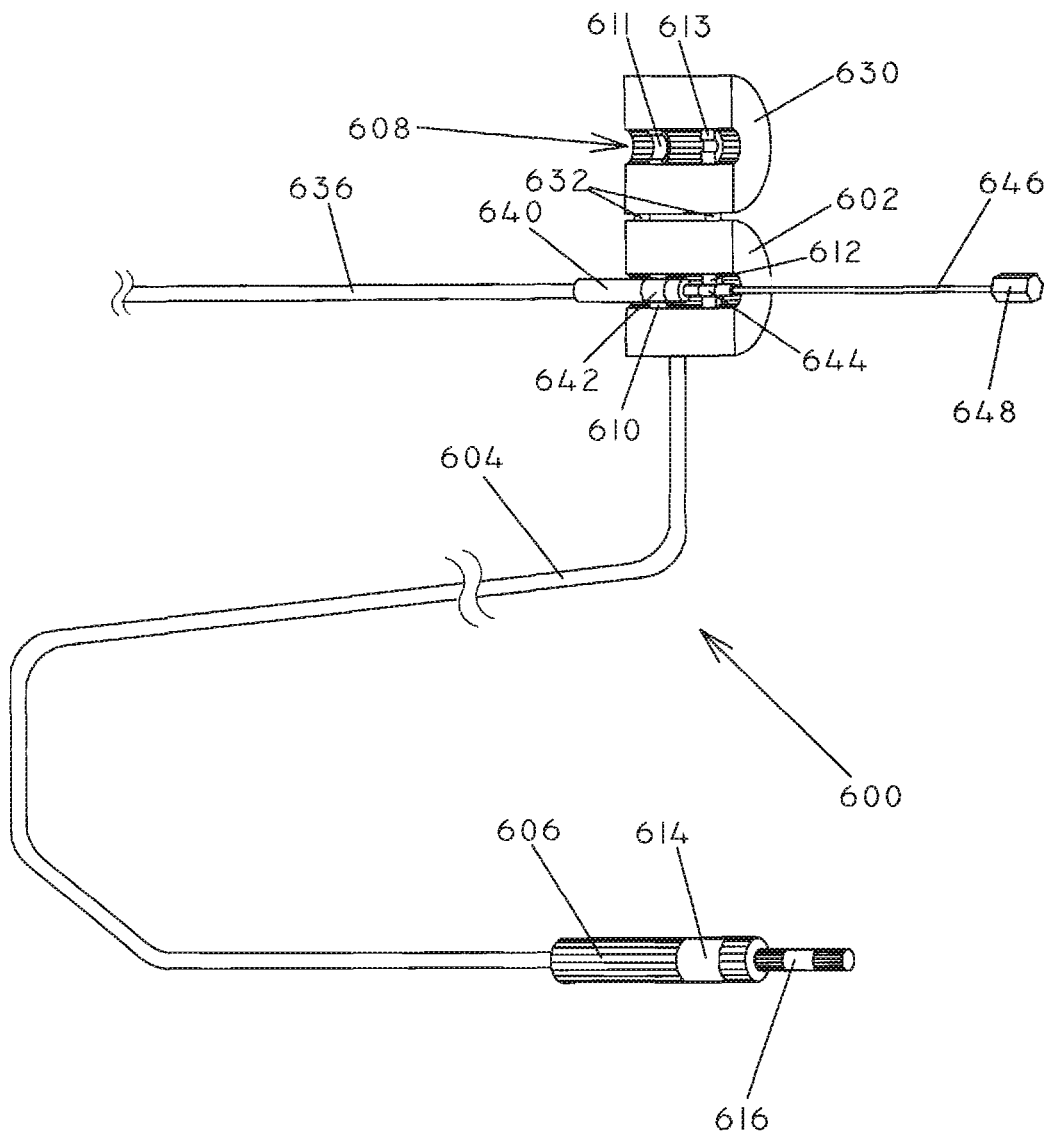
FIG. 9 is a schematic view of a stimulation lead connection adapter in accordance with another embodiment of the invention.

Referring now to FIG. 9, another embodiment of a stimulation lead connection adapter 600 is shown. In this embodiment, a cylindrical two-part housing (602 and 630) defines a lead socket 608. The two housing parts (602 and 630) are joined by hinges 632 and can be closed together so that the housing parts surround the sides of the lead socket 608. The lead socket 608 is configured so as to accommodate the proximal end 640 of a stimulation lead 636. The dimensions of the lead socket 608 can be selected so as to accommodate different types of stimulation leads. One or more electrical contacts (such as 610 and 612) can be disposed along the lead socket 608 and configured to make contact with conductors (642 and 644) on the proximal end 640 of a stimulation lead 636. The stimulation lead connection adapter 600 can also include a connector 604. The connector 604 connects the housing parts 602 and 630 with an adapter plug 606. The adapter plug 606 can include one or more conductors (such as 614 and 616). The connector 604 can provide electrical communication between electrical contacts along the lead socket 608 and conductors on the adapter plug 606.

Various configurations of stimulation lead connection adapters are included amongst embodiments of the invention. In some embodiments, such as those shown in FIGS. 2-9, the housing of the stimulation lead connection adapter may take on a clam-shell type configuration where the proximal end of the stimulation lead is inserted into the lead socket of the adapter housing from the side. However, in other embodiments, the housing of the stimulation lead connection adapter may take on a configuration that allows the insertion of the proximal end of the stimulation lead into the lead socket from an end of the stimulation lead connection adapter.

Figure 10:
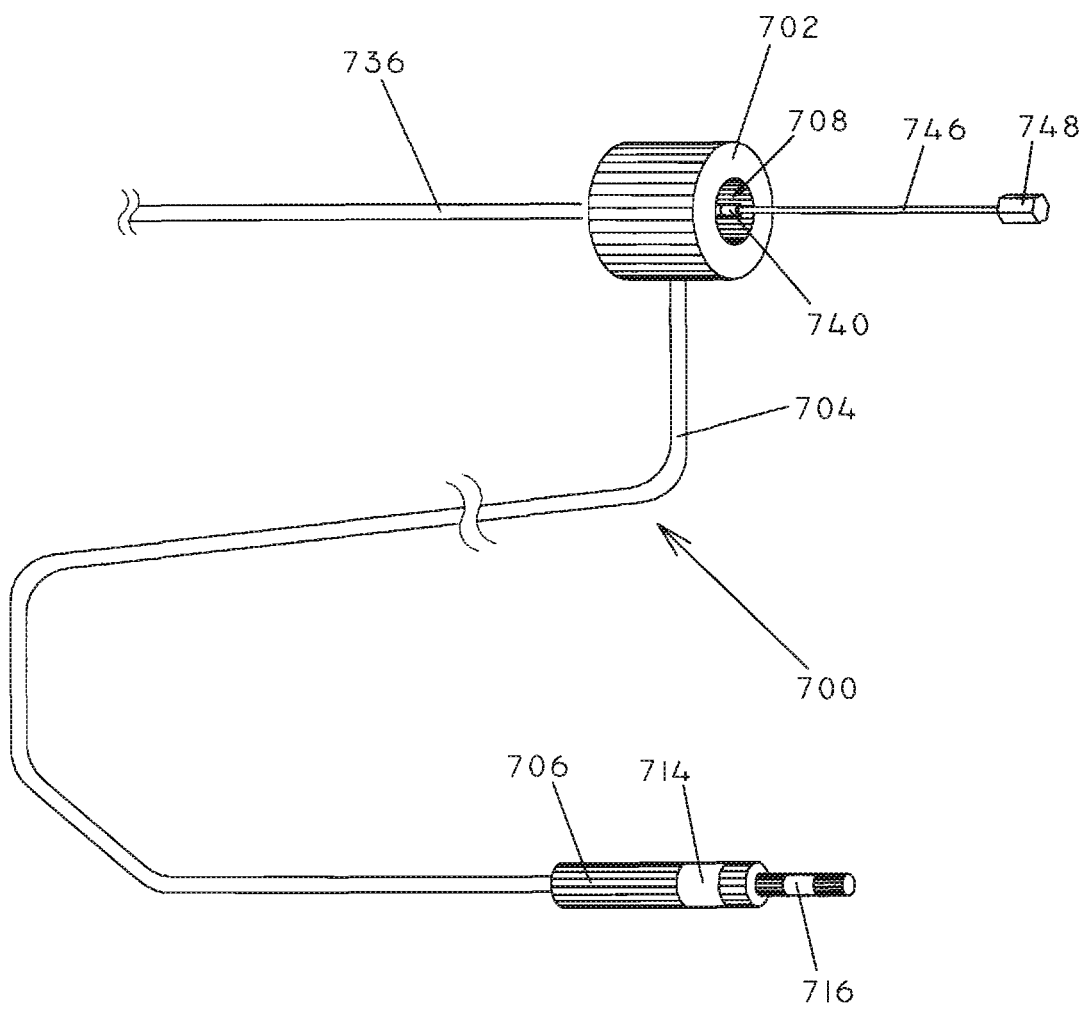
FIG. 10 is a schematic view of a stimulation lead connection adapter in accordance with another embodiment of the invention.

Referring now to FIG. 10, an embodiment of a stimulation lead connection adapter 700 is shown configured to allow insertion of the proximal end of a stimulation lead from the end of the housing 702. A housing 702 defines a lead socket 708. In this embodiment, the lead socket 708 is configured as the lumen of a housing 702 that is cylindrical in structure. However, the housing can take on other shapes as well such as toroidal, columnar, polygonal, and the like. The lead socket 708 is configured so as to accommodate the proximal end of a stimulation lead 736. Specifically, the lead socket 708 is configured so as to allow the passage of the proximal end of the stimulation lead 736 along with a stylet 746 or guide wire and an end cap 748 used for manipulating the stylet 746. The specific dimensions of the lead socket 708 can be selected so as to accommodate different types of stimulation leads. One or more electrical contacts (not shown) can be disposed along the lead socket 708 and configured to make contact with conductors on the proximal end of the stimulation lead 736. The stimulation lead connection adapter 700 can also include a connector 704. The connector 704 connects the housing 702 with an adapter plug 706. The adapter plug 706 can include one or more conductors (such as 714 and 716). The connector 704 can provide electrical communication between electrical contacts along the lead socket 708 and conductors on the adapter plug 706.

Figure 11:
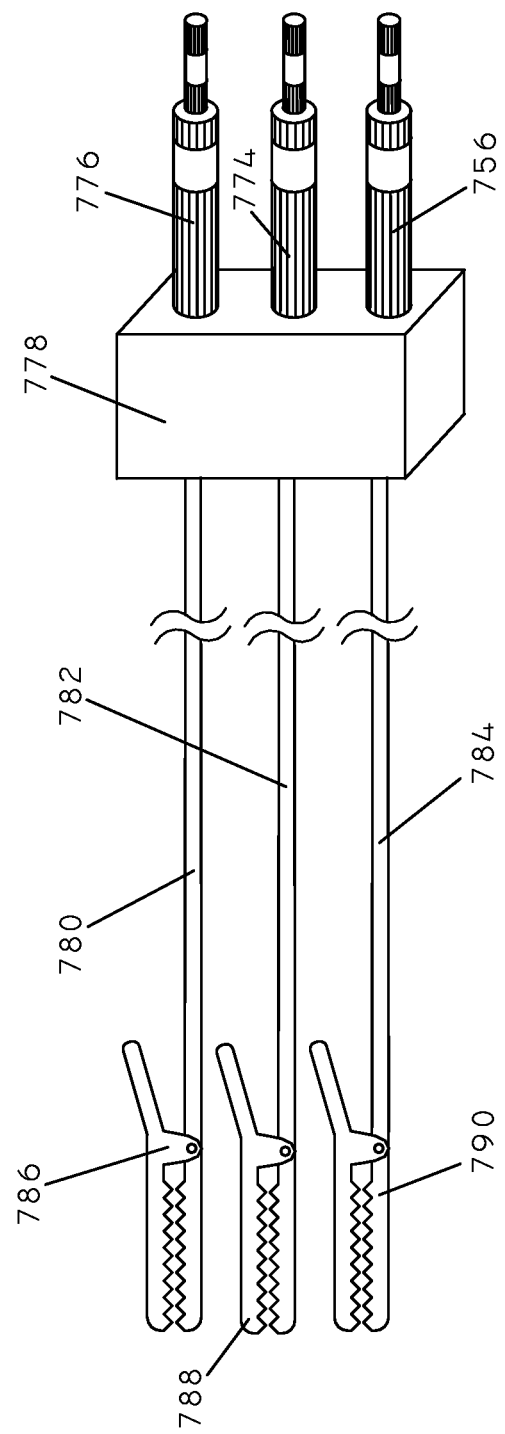
FIG. 11 is a schematic view of a stimulation lead connection adapter in accordance with another embodiment of the invention.

It will be appreciated that lead sockets of the adapter can take on various configurations. By way of example, referring now to FIG. 11, an embodiment of a stimulation lead connection adapter is shown in accordance with another embodiment of the invention, wherein the stimulation lead socket is configured as an alligator type clip. In this embodiment, a first clip 786 is in electrical communication with a first adapter plug 776 via a first connector 780. A second clip 788 is in electrical communication with a second adapter plug 774 via a second connector 782. A third clip 790 is in electrical communication with a third adapter plug 756 via a third connector 784. In some embodiments, a protective shroud (not shown) can positioned over the clips. The adapter plugs are attached to a manifold retention block 778 that maintains the spacing and orientation of the adapter plugs with respect to one another. Specifically, the manifold retention block 778 functions to position the adapter plugs so that they can be easily inserted into the receiving portion of an implantable medical device, such as the header.

In some embodiments, the invention includes an implantable medical device that is configured to conduct some or all of the functions normally handled by a PSA. As such, a stimulation lead adapter can be used to connect a stimulation lead to an implantable medical device that itself is configured to perform desirable functions, such as testing, normally conducted by a PSA system.

Figure 12:
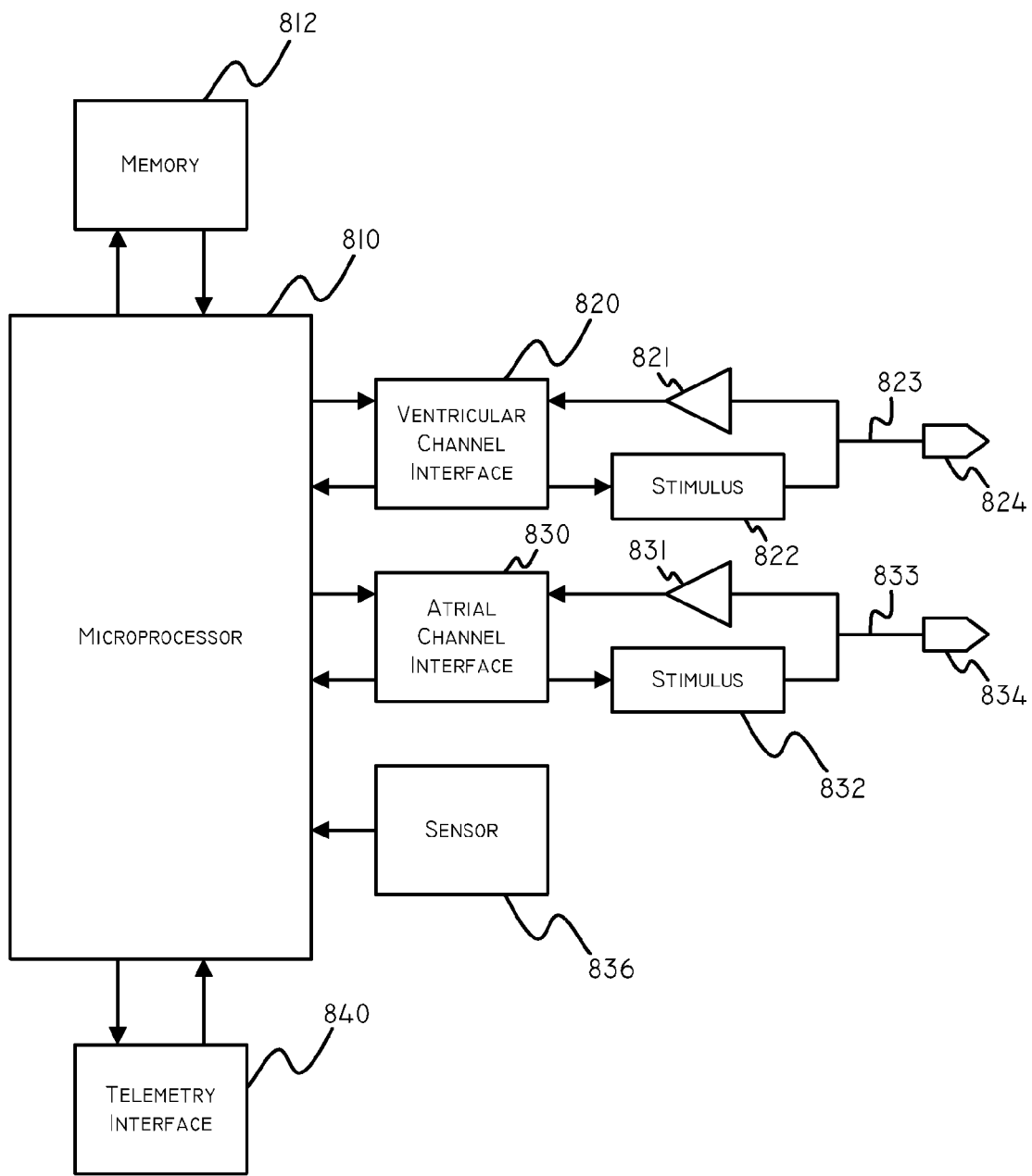
FIG. 12 is a diagram of an implantable medical device in accordance with an embodiment of the invention.

A particular implementation of an implantable medical device that can be configured to perform PSA functions is shown in FIG. 12. In this case, the implantable medical device is a pacemaker. As used herein, the term pacemaker should be taken to mean any cardiac rhythm management device with a pacing functionality including an implantable cardioverter/defibrillator that includes pacing functionality. A controller senses cardiac events through a sensing channel and outputs pacing pulses to the heart via a pacing channel in accordance with a programmed pacing mode. A microprocessor 810 serves as the controller in this embodiment and communicates with a memory 812 via a bidirectional data bus. The memory 812 typically comprises a ROM or RAM for program storage and a RAM for data storage.

The implantable medical device has atrial sensing and pacing channels comprising electrode 834, lead 833, sensing amplifier 831, output circuit 832, and an atrial channel interface 830 which communicates bidirectionally with a port of microprocessor 810. In this embodiment, the device also has ventricular sensing and pacing channels comprising electrodes 824, lead 823, sensing amplifier 821, output circuit 822, and ventricular channel interface 820. For each channel, the same lead and electrode are used for both sensing and pacing. The channel interfaces 820 and 830 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. The implantable medical device can also include one or more sensors 836, such as an accelerometer, a posture sensor, an impedance sensor, a minute ventilation sensor, a pressure sensor, or the like. A telemetry interface 840 is also provided for communicating with an external programmer.

The implantable medical device can be configured to performed PSA functionality. For example, programs to execute PSA functions can be stored in memory 812 and then executed by the microprocessor 810. PSA functions can specifically include: determining in situ lead impedance, diaphragmatic capture testing, capture threshold (voltage and/or current) testing, P wave and R wave amplitude and slew rate testing, Wenckebach test, and in vivo V-A retrograde conduction time testing. PSA functionality can also specifically include: temporary pacing under DDD, DDI, DOO, VVI, VDD, VOO, AAI, or AOO modalities; high-rate pacing (sometimes referred to as anti-tachycardia pacing), rapid total output inhibition, and emergency VVI pacing.

In situ lead impedance can be affected by various factors including the tissue surrounding the electrode(s), the physical configuration of the electrode(s), and the particular current/voltage used for stimulation. Care providers frequently want to measure the in situ lead impedance during or after the process of placing the lead into position within the heart. In some cases, lead impedance can be used as an indicator of whether or not the leads need to be repositioned. In some embodiments, an implantable medical device is included that is configured to calculate the in situ lead impedance. Lead impedance can be calculated according to Ohm's law based on the known current (Amps) and the known electrical potential (Volts). Components of the implantable CRM device such as the controller and/or the microprocessor can be configured to perform this calculation.

Depending on the precise placement of stimulation leads within the heart and the amplitude of stimulation delivered, it is possible to inadvertently stimulate the diaphragm with pacing pulses. Inadvertent stimulation of the diaphragm can cause discomfort for a patient and may interrupt normal breathing patterns. As such, it is desirable to perform testing when the stimulation leads are being implanted in order to make sure that the diaphragm is not inadvertently stimulated. Many pacing devices provide stimulation pulses with an electrical potential amplitude of not more than about 6 Volts. However, it can be desirable to provide a margin of safety and test at a higher voltage that will be actually used in practice. As such, many PSA systems include the ability to test for capture of the diaphragm by delivering stimulation pulses at an electrical potential equal to about 10 Volts. In some embodiments, the invention includes an implantable medical device, such as an implantable CRM device, that can deliver electrical stimulation pulses at an electrical potential larger than that associated with normal pacing pulses. In an embodiment, the invention includes an implantable CRM device that is configured to deliver pulses of electrical stimulation at a magnitude of about 10 Volts or more. For example, the output circuits 832 and/or 822 can be configured to deliver pulses of electrical stimulation at a magnitude of about 10 Volts or more.

Capture threshold testing is a function that can be performed by a PSA in order to determine the voltage and/or current that is necessary to effectively capture the desired cardiac chamber, such as the atria or the ventricles. In one method of capture threshold testing, a test pulse is delivered at an amplitude that is thought to be sufficient to capture the desired tissue. After capture is verified, then the amplitude (current or electrical potential) is reduced and test pulses are delivered again followed by monitoring for capture. This process continues on reducing the amplitude until the desired cardiac chamber is no longer captured. In some cases, the threshold testing can also proceed in the opposite direction. For example, the test pulses can start at a low amplitude that is insufficient to capture the desired cardiac chamber and then be increased until capture is detected. In an embodiment, the invention includes an implantable CRM device that is configured to perform threshold testing (current or electrical potential) of a desired chamber of the heart. By way of example, the controller and/or microprocessor can be configured to perform capture threshold testing.

Aspects of the cardiac ECG or electrogram such as wave form details can typically be determined by a PSA. For example, P wave and/or R wave amplitudes and slew rates are parameters that can be determined by some PSA systems. The P wave of an ECG or electrogram is generated by activation of the atria. The R wave is produced by activation of both ventricles. The amplitude and the slew rate of both the P wave and R wave can provide valuable diagnostic information to a care provider. In an embodiment, the invention includes an implantable CRM device that is configured to determine the amplitude and/or slew rate of the P wave and/or the R wave. By way of example, the controller and/or microprocessor can be configured to determine the amplitude and/or slew rate of the P wave and/or the R wave and then this information can be output through the telemetry interface.

In the normal heart, an impulse from the atria is conducted through the AV Node and the His-Purkinje system in order to reach the tissue of the ventricle and trigger ventricular contraction. This signal pathway can function to maintain synchrony between the contractions of the atria and contractions of the ventricles. However, when the atria exceed a threshold contraction rate, the ventricles typically stop responding to further increases in atrial contraction rate and independently assume a slower rate of contraction. This threshold contraction rate can be referred to as the "Wenckebach rate" and is believed to be caused by refractoriness of the AV Node. Many PSA systems can perform testing to determine at what point ventricular contractions fail to keep pace (in a 1:1 ratio) with atrial contractions. This is sometimes referred to as "Wenckebach testing" and involves pacing the atria at increasingly faster speeds while monitoring ventricular contractions in order to determine when the ventricles fail to continue to increase their contraction rate along with the atria at a 1:1 ratio. In an embodiment, the invention includes an implantable CRM device that is configured to perform Wenckebach testing. By way of example, the controller and/or microprocessor can be configured to perform Wenckebach testing.

Retrograde conduction refers to the transmission of a depolarizing impulse from the ventricles to the atria. Retrograde conduction can also be referred to as ventriculoatrial (VA) conduction or retrograde VA conduction. Retrograde VA conduction is clinically significant because when it is present in a patient it may predispose the patient to pacemaker-induced tachycardia when DDD pacing is employed. In an embodiment, the invention includes an implantable CRM device that can assess whether or not a patient experiences retrograde VA conduction. In an embodiment, the invention includes a CRM device that can determine retrograde VA conduction time, that is, the time between when a stimulation pulse is delivered to a ventricle and when that stimulation pulse can be detected within an atrium. By way of example, the controller and/or microprocessor can be configured to determine retrograde VA conduction time.

Embodiments of the invention can be used to deliver temporary pacing therapy under DDD, DDI, DOO, VVI, VDD, VOO, AAI, or AOO modalities. For example, an implanted CRM device can be attached to a stimulation lead using a stimulation lead adapter in accordance with an embodiment of the invention. The implanted CRM device, and components thereof such as the controller, microprocessor, and output circuit(s), can be configured to deliver stimulation pulses in accordance with a desirable modality, such as any of the modalities named above.

In addition to temporary pacing therapy, embodiments of the invention can also be used to deliver relatively high-rate pacing, sometimes referred to as anti-tachycardia pacing. In some embodiments, pacing can be delivered by the implanted CRM device at a rate greater than or equal to 200 pulses per minute. In some embodiments, pacing can be delivered by the implanted CRM device at a rate greater than or equal to 400 pulses per minute. In some embodiments, pacing can be delivered by the implanted CRM device at a rate greater than or equal to 600 pulses per minute. In some embodiments, pacing can be delivered by the implanted CRM device at a rate up to 1000 pulses per minute.

Sometimes it can be desirable to be able to quickly shut-off all output passing through the stimulation leads. This feature is sometimes referred to as rapid total output inhibition in the context of PSA systems. In an embodiment, the implanted CRM device can be configured to allow for rapid total output inhibition. Specifically, components of the CRM device, such as an output circuit and/or a controller can be configured to rapidly shut off output.

Sometimes it can be desirable to be able to quickly engage pacing in the VVI mode. This feature is sometimes referred to as emergency VVI pacing in the context of PSA systems. In an embodiment, the implanted CRM device can be configured to allow for emergency VVI pacing. Specifically, components of the CRM device, such as an output circuit, and/or a controller or microprocessor can be configured to rapidly begin delivering pacing in the VVI mode along with the related settings associated emergency VVI pacing including faster rate, relatively high output voltage, relatively long pulse width, and the like.

Embodiments of the invention can also include methods of using an implantable medical device, such as a CRM device, to perform tasks normally conducted with a PSA. For example, in an embodiment, the method includes the steps of inserting a stimulation lead into a patient and attaching the proximal end of the stimulation lead to an implantable medical device with a stimulation lead adapter, such as those described herein. The method can also include the step of performing pacing system analyzer functions with the implantable medical device such as one or more of the pacing system analyzer functions described herein.

In some embodiments, a circuit can be included with a stimulation lead connection adapter that can be controlled by a CRM device in order to deliver stimulation pulses at a magnitude greater than those delivered by the CRM device itself. As such, in some embodiments a stimulation lead connection adapter can be configured to allow a CRM device to perform diaphragmatic capture testing though the CRM device itself may not have the capability of generating pacing pulses with a sufficiently high amplitude. For example, the adapter itself can include an output circuit such as a pacing circuit configured to deliver individual stimulation pulses at magnitudes of greater than 6V in response to certain output received from the CRM device. In various embodiments the adapter can include a sensor circuit to detect an electrical stimulation pulse from a CRM device and an output circuit to generate stimulation pulses at magnitudes of 10 Volts or more. In some embodiments the output circuit can include a power supply. In some embodiments the power supply can include a battery and/or a capacitor.

Figure 13:
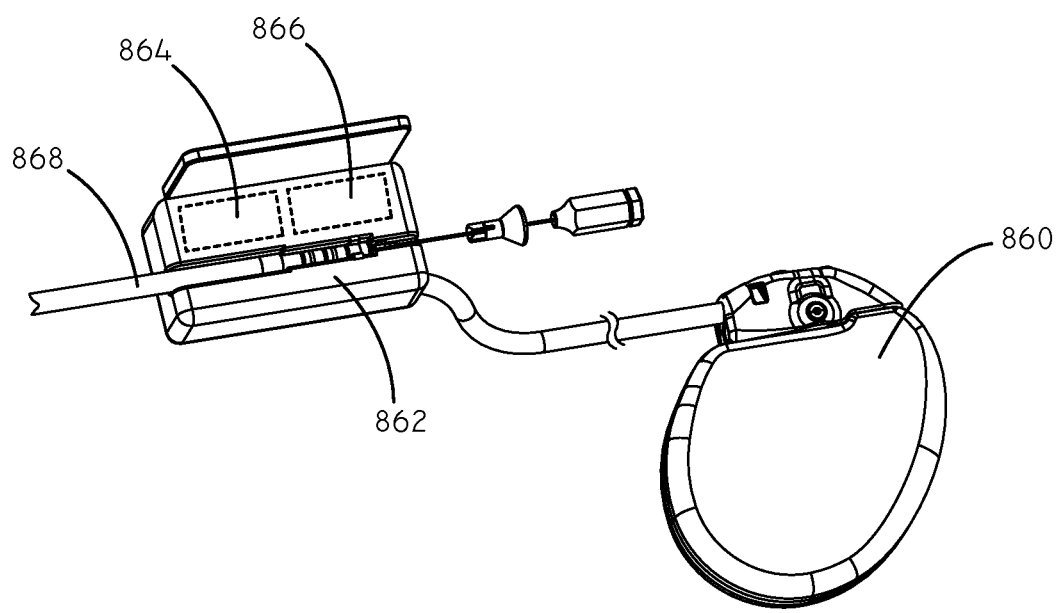
FIG. 13 is a schematic view of a stimulation lead connection adapter in accordance with another embodiment of the invention.

Referring now to FIG. 13, a schematic view is shown of a stimulation lead connection adapter 862 in accordance with another embodiment of the invention. A CRM device 860 is coupled to the stimulation lead connection adapter 862, which is in turn connected to a stimulation lead 868. The stimulation lead connection adapter 862 can include an output circuit 864 and a sensor circuit 866. The sensor circuit 866 can be configured to detect electrical signals from the CRM device 860. In some embodiments, the sensor circuit 866 can be configured to detect electrical signals from a separate external device, such as a PSA. In some embodiments the sensor circuit can include various electrical components such as amplifiers, filters, converters, signal processors, and the like. The output circuit 864 can be configured to generate one or more stimulation pulses at an amplitude of greater than about 6 Volts and in some embodiments greater than about 10 Volts in response to detected electrical signals from the CRM device 860. The stimulation pulses can then be delivered to a target tissue through the stimulation lead 868. In some embodiments the output circuit can include various electrical components such as a power supply (e.g., battery and/or a capacitor), filter, waveform generator, and the like.

Implantable CRM devices in various embodiments of the invention can include telemetry functionality that can be used to deliver data from the implantable CRM device, such as PSA function data, to an external unit, sometimes referred to as a programmer. Such telemetry can occur through various techniques including radiofrequency transmission, induction, sound waves, and the like.

Figure 14:
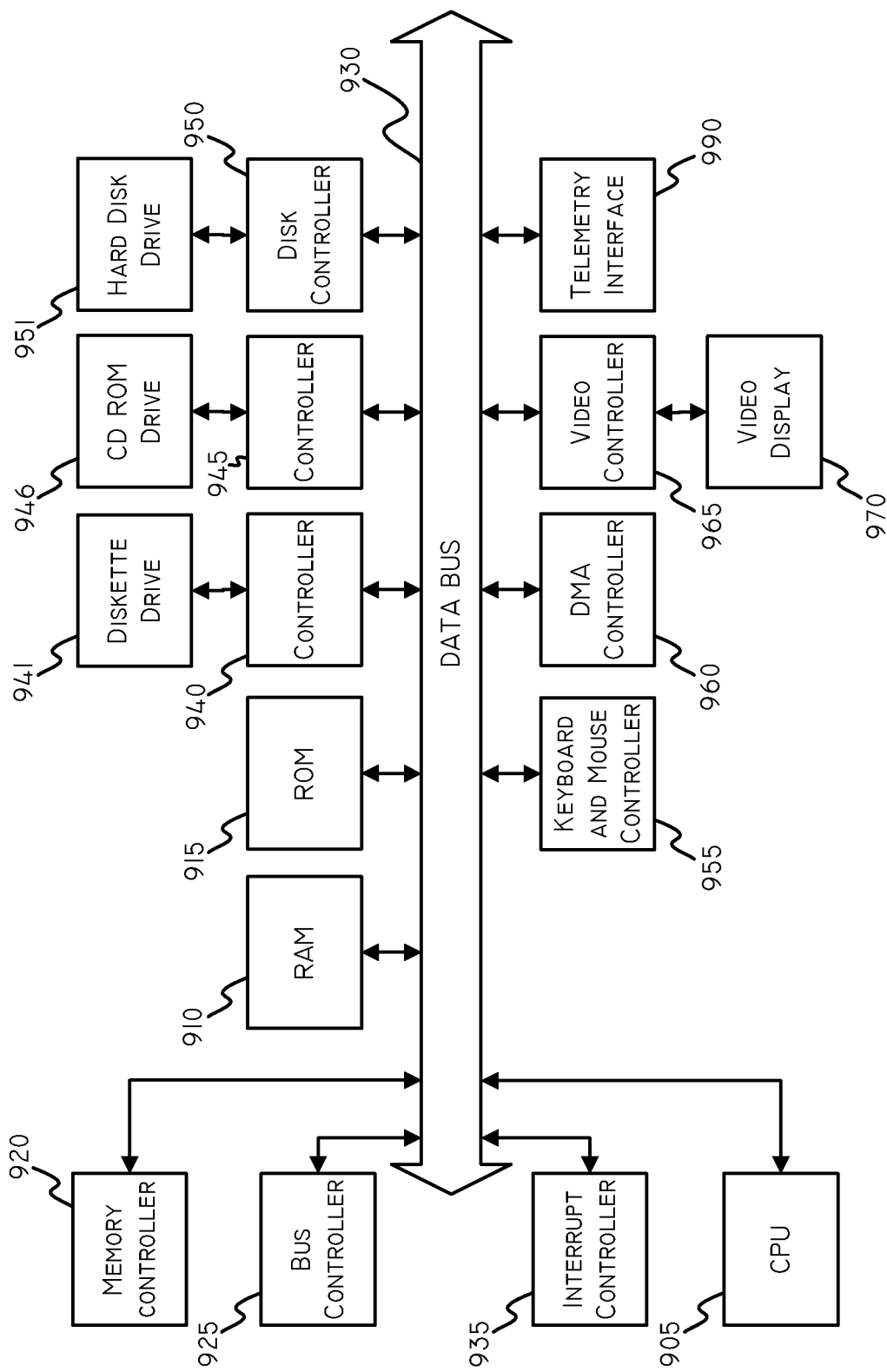
FIG. 14 is a diagram of various programmer components in accordance with an embodiment of the invention.

Exemplary programmers include the Model 2920 Programmer and Model 3120 Programmer, both available from Boston Scientific Corporation, Natick, Mass. Programmers can include components common to many computing devices. Referring now to FIG. 14, a diagram of various programmer components is shown in accordance with an embodiment of the invention. The programmer system includes a central processing unit (CPU) 905, which may include a conventional microprocessor, random access memory (RAM) 910 for temporary storage of information, and read only memory (ROM) 915 for permanent storage of information. A memory controller 920 is provided for controlling system RAM 910. A bus controller 925 is provided for controlling data bus 930, and an interrupt controller 935 is used for receiving and processing various interrupt signals from the other system components.

Mass storage may be provided by diskette drive 941, which is connected to bus 930 by controller 940, CD-ROM drive 946, which is connected to bus 930 by controller 945, and hard disk drive 951, which is connected to bus 930 by controller 950. User input to the programmer system may be provided by a number of devices. For example, a keyboard and mouse can connected to bus 930 by keyboard and mouse controller 955. DMA controller 960 is provided for performing direct memory access to system RAM 910. A visual display is generated by a video controller 965, which controls video display 970. Programmer system can also include a telemetry interface 990 which allows the programmer system to interface and exchange data with an implantable medical device.

In some embodiments of the invention, the programmer system can be configured to display data to a care provider in a manner that would be familiar to them if they are used to the data typically displayed by a PSA system. For example, in some embodiments, the invention can include a programmer device that is configured to display all PSA-related data on a single screen so that a care provider can simply access one screen within the programmer software and have access to all PSA-like functionality. In some embodiments, all PSA-related data is displayed together on one tab of a programmer software screen.

Figure 15:
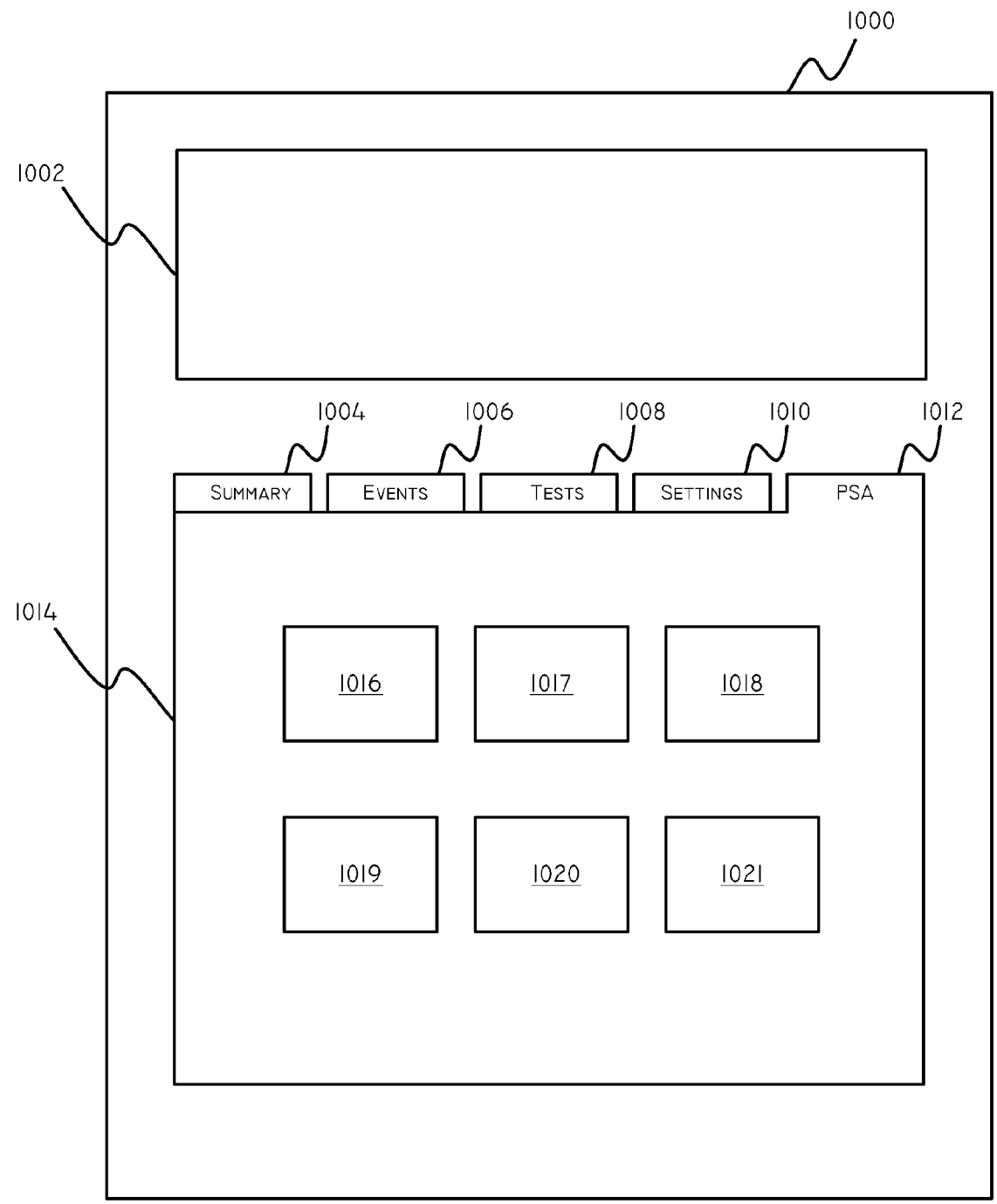
FIG. 15 is an image of a programmer graphical user interface screen in accordance with an embodiment of the invention.

Referring now to FIG. 15, a schematic view of a programmer graphical user interface screen 1000 is shown in accordance with an embodiment of the invention. The user interface screen 1000 can include a first display box 1002 that can display various information related to the status of the patient include electrogram traces, basic physiological data such as heart rate, and the like. The user interface screen 1000 can also include a second display box 1014 that is associated with a plurality of tabs (1004, 1006, 1008, 1010, and 1012). The tabs can be used in order to select what data is shown within the second display box 1014. A particular tab 1012 can be used to access data that is customarily associated with data generated and displayed by a PSA system. It is believed that grouping data customarily associated with a PSA system under one tab can make the use of the programmer more user-friendly for those who are accustomed to using dedicated PSA systems. Various pieces of information can be displayed within boxes (1016, 1017, 1018, 1019, 1020, and 1021) in the second display box 1014. Such data can include, for example, PSA function data such as threshold test data, lead impedance data, slew rate data, and 10 Volt pacing data.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A stimulation lead adapter comprising:
 a housing having a first end and a second end opposite the first, and a stimulation lead socket within the housing configured to electrically engage and retain the proximal end of a stimulation lead,
 the stimulation lead socket comprising a first end and a second end disposed on opposite sides of a lengthwise major axis, the stimulation lead socket defining a first aperture in the first end, a second aperture in the second end, and an open channel between the first aperture and the second aperture, the open channel extending between the first end of the housing and the second end of the housing;
 the stimulation lead socket further comprising a side wall connecting the first end of the lead socket with the second end of the lead socket; and
 a first electrical contact disposed along the side wall of the stimulation lead socket, the first electrical contact configured to electrically engage the proximal end of a stimulation lead;
 an adapter plug configured to electrically engage a stimulation lead port of an implantable medical device;
 a connector configured to provide electrical communication between the stimulation lead socket and the adapter plug, the connector configured to allow movement of the adapter plug independent of the stimulation lead socket; and
 a cover configured to fit over the stimulation lead socket, the cover configured to move between an open position and a closed position.

2. The stimulation lead adapter of claim 1, the stimulation lead socket configured to electrically engage and retain the proximal end of a stimulation lead having a stylet and/or a guide wire disposed therein.

3. The stimulation lead adapter of claim 1, the side wall surrounding less than all of the stimulation lead socket axially around the major axis.

4. The stimulation lead adapter of claim 1, further comprising a cover configured to fit over the side wall of the stimulation lead socket.

5. The stimulation lead adapter of claim 1, the stimulation lead socket comprising an attachment structure configured to secure the proximal end of a stimulation lead inserted from a direction perpendicular to the major axis.

6. The stimulation lead adapter of claim 1, the mechanical fastener comprising an electrical contact.

7. The stimulation lead adapter of claim 1, the stimulation lead socket comprising an alligator clip.

8. The stimulation lead adapter of claim 1, comprising a plurality of stimulation lead sockets.

9. The stimulation lead adapter of claim 1, comprising a plurality of adapter plugs.

10. The stimulation lead adapter of claim 1, further comprising a manifold retention block configured to retain a plurality of adapter plugs together.

11. The stimulation lead adapter of claim 1, the connector comprising a wire and a polymeric sheath disposed over the wire.

12. The stimulation lead adapter of claim 1, further comprising a sensor circuit configured to detect an electrical signal and an output circuit configured to generate a stimulation pulse with an amplitude of greater than 6 Volts in response to a detected electrical signal.

13. The stimulation lead adapter of claim 1, wherein the mechanical fastener comprises a conductive material and provides electrical communication between the stimulation lead and other components of the stimulation lead adapter.

* * * * *